(12) United States Patent
Frank

(10) Patent No.: US 6,500,165 B1
(45) Date of Patent: Dec. 31, 2002

(54) ACTIVE ANTISEPSIS DEVICE

(76) Inventor: Steven R. Frank, 11192 Twin Spruce Rd., Golden, CO (US) 80403

( * ) Notice: Subject to any disclaimer, the term of this patent is extended or adjusted under 35 U.S.C. 154(b) by 0 days.

(21) Appl. No.: 09/718,519

(22) Filed: Nov. 21, 2000

Related U.S. Application Data

(63) Continuation of application No. 09/182,581, filed on Oct. 29, 1998, now abandoned.

(51) Int. Cl.[7] ............................................... A61M 31/00
(52) U.S. Cl. ........................ 604/502; 604/20; 604/891.1
(58) Field of Search ........................... 604/20, 19, 890.1, 604/891.1, 500, 501, 502, 289, 290, 304

(56) References Cited

U.S. PATENT DOCUMENTS

| | | |
|---|---|---|
| 3,831,598 A | 8/1974 | Tice |
| 3,918,459 A | 11/1975 | Horn |
| 3,964,477 A | 6/1976 | Ellis et al. |
| 4,305,390 A | 12/1981 | Swartz |
| 4,411,648 A | 10/1983 | Davis et al. |
| 4,474,570 A | 10/1984 | Ariura et al. |
| 4,774,833 A | 10/1988 | Weibler et al. |
| 4,821,700 A | 4/1989 | Weibler et al. |
| 5,306,287 A | 4/1994 | Becker |
| 5,322,520 A | 6/1994 | Milder |
| 5,328,451 A | 7/1994 | Davis et al. |
| 5,498,248 A | 3/1996 | Milder |
| 5,551,953 A * | 9/1996 | Lattin et al. .................. 604/20 |
| 5,571,149 A | 11/1996 | Liss et al. |
| 5,676,648 A | 10/1997 | Henley |
| 5,749,845 A | 5/1998 | Hildebrand et al. |
| 5,846,217 A | 12/1998 | Beck et al. |
| 5,865,787 A | 2/1999 | Shapland et al. |
| 6,001,088 A | 12/1999 | Roberts et al. |
| 6,282,444 B1 * | 8/2001 | Kroll et al. .................. 607/120 |
| 6,349,232 B1 * | 2/2002 | Gordon ...................... 604/132 |
| 6,402,689 B1 * | 6/2002 | Scarantino et al. ......... 128/903 |
| 6,416,531 B2 * | 7/2002 | Chen .......................... 128/898 |

OTHER PUBLICATIONS

Electric silver antisepsis. A.A. marino, E.A. Deitch & J.A. Albright. IEEE Trans. Biomed.Eng. BME–32:336–337, 1985.*

* cited by examiner

Primary Examiner—Brian L. Casler
Assistant Examiner—Jeremy Thissell

(57) ABSTRACT

A device for maintaining antisepsis of embedded devices with a body is provided. The device comprises a housing having a first active surface and a second active surface with the housing being sized and shaped for being received within the body. The first active surface and the second active surface are contactable with the tissue and bodily fluids. A metal antimicrobial substance is attached to at least a portion of the first active surface and the second active surface. A control system is electrically connected to the first active surface and the second active surface of the housing for creating an electric field between the first active surface and the second active surface through the body with the electric field ionizing the antimicrobial substance thereby profusing the substance into the tissue.

15 Claims, 6 Drawing Sheets

ACTIVE ANTISEPSIS DEVICE

The present application is a continuation of pending patent application Ser. No. 09/182,581, filed on Oct. 29, 1998, now abandoned entitled "Electrolytic Substance Infusion Device".

BACKGROUND OF THE INVENTION

1. Field of the Invention

The present invention relates generally to a treatment device for medical application to body tissue for maintaining antisepsis in long-term indwelling medical devices and, more particularly, it relates to a treatment device which electrolytically infuses silver ions from the surface of an indwelling device into the surrounding tissues under remote control and power delivery from an external source thereby providing an means of long-term antisepsis which is active and controlled.

2. Description of the Prior Art

There have been attempts in the past to develop hydrophilic or lubricious coatings, thrombo-resistant coatings, antibiotic coatings, and even metallic coatings for long-term indwelling medical devices. These attempts have been in an effort to deal with the pervasive issue of sepsis in indwelling medical devices caused primarily by the surface colonization of biofilms. Biofilms are layers or colonies of bacteria which adhere to a foreign surface and protect themselves with a slime layer rendering the bacteria that breed within the slime thousands of times more resistant to known antibacterial agents.

The hydrophilic and lubricious coatings seek to stop the adhering of these films and thus thwart the development of the colonies. The thrombo-resistant coatings seek to resist the protein layer build-ups that can host the colonies. The metallic coatings and antibiotic coatings seek to kill the bacteria as they attach. Unfortunately, the coatings have quite clearly failed for various reasons to provide sufficient protection by any of those means. Sepsis of indwelling devices (catheters, ports, prosthetic joints, meshes, and shunts) still range from 5% to 15%.

The failure of these techniques rests in part on the fact that these techniques are all passive. That is to say, the techniques do not force interaction between the surface and the bacteria. A silver coated surface elutes too slowly to repel or effectively inhibit the colonizing bacteria. While special silver coatings have been developed which have high rates of elution, the silver coatings exhaust their capability frivolously in a few days by continuously eluting at rates that cannot be sustained. Antibiotic coatings effectively kill the layer of colonizing bacteria that adhere to the surface. Ironically, this activity is its own un-doing as the dead bacteria serve as an insulating layer to protect and facilitate adherence of the next layer. None of the existing systems offer any means for effectively penetrating the biofilm layer that protects the bacterial colonies and hence offers extremely limited effectivity.

Additionally, since the release of agent from these existing technologies is dependant upon the interstitial environment, the dose over time changes in some unknown manner varying with the person, with time, and with the adherence of proteins. As a fibrin sheath builds up on the surface and the material elutes in rates determined by the physiology of the particular surrounding tissue and individual, the actual dose, rate, and effectiveness diminish and become unknown. This renders the present techniques quite ineffective and difficult or impossible to clinically verify.

SUMMARY

The present invention is a device for maintaining antisepsis of tissue of a body. The device comprises at least a first active surface contactable with the tissue and at least a second active surface contactable with the tissue. A control system is electrically connected to the first active surface and the second active surface with the control system creating an electric field between the first active surface and the second active surface through the body. Silver, an antimicrobial substance, is on or comprised of at least a portion of the first active surface with the substance being ionized upon application of the electric field thereby profusing the substance into the tissue.

In yet another embodiment of the present invention, the device further comprises using a bipolar field at low frequencies allowing both the first active surface and the second active surface to act as anodes. Preferably, the device further comprises using a bipolar field at low frequencies to maintain a surface only distribution of the substance.

In still another embodiment of the present invention, the method further comprises providing an embedded microcontroller or other control circuitry for controlling the delivery rate of the substance, dose of the substance, and selected active surfaces.

In these embodiments, the therapeutic protocol administered by the embedded microcontroller is controller by embedded firmware within the implanted device. Alternately, the therapeutic protocol is modified or communicated entirely through the modulation of the applied electromagnetic signal. The electromagnetic signal serves to allow communication to the embedded microcontroller, which is controlling the administration of silver ions, and to provide power for the operation of the system. This is accomplished by modulating the RF electromagnetic field, which is being applied to the system transcutaneously. The modulation of the applied field is detected by the circuitry of the system and then de-coded by the microcontroller. The modulation could be amplitude based, frequency shift keying based, phase shift keying or any other modulation technique known to one skilled in the art.

The system of the present invention derives power from this applied RF electromagnetic field, an internal battery, or any other power source. The system then generates the higher voltages necessary to force the ionization of silver from the active surface surfaces and the penetration into the surrounding tissue or biofilms by means of a controllable DC-to-DC converter. The converter is operated by the embedded microcontroller and can be adjusted in real-time to produce the required waveforms.

In the case of a battery operated system, the system is pre-programmed to come out of a stand-by mode (wake-up) and operate, treating the surrounding tissue according to the protocol required for the particular application. After treatment (typically five (5) to fifteen (15) minutes) the system goes back to sleep (stand-by) thus conserving battery power and surface silver until it is required to operate again. This can be daily, or weekly depending on the expected re-colonization rate of the device.

DETAILED DESCRIPTION OF THE PREFERRED EMBODIMENTS

Figure 1:
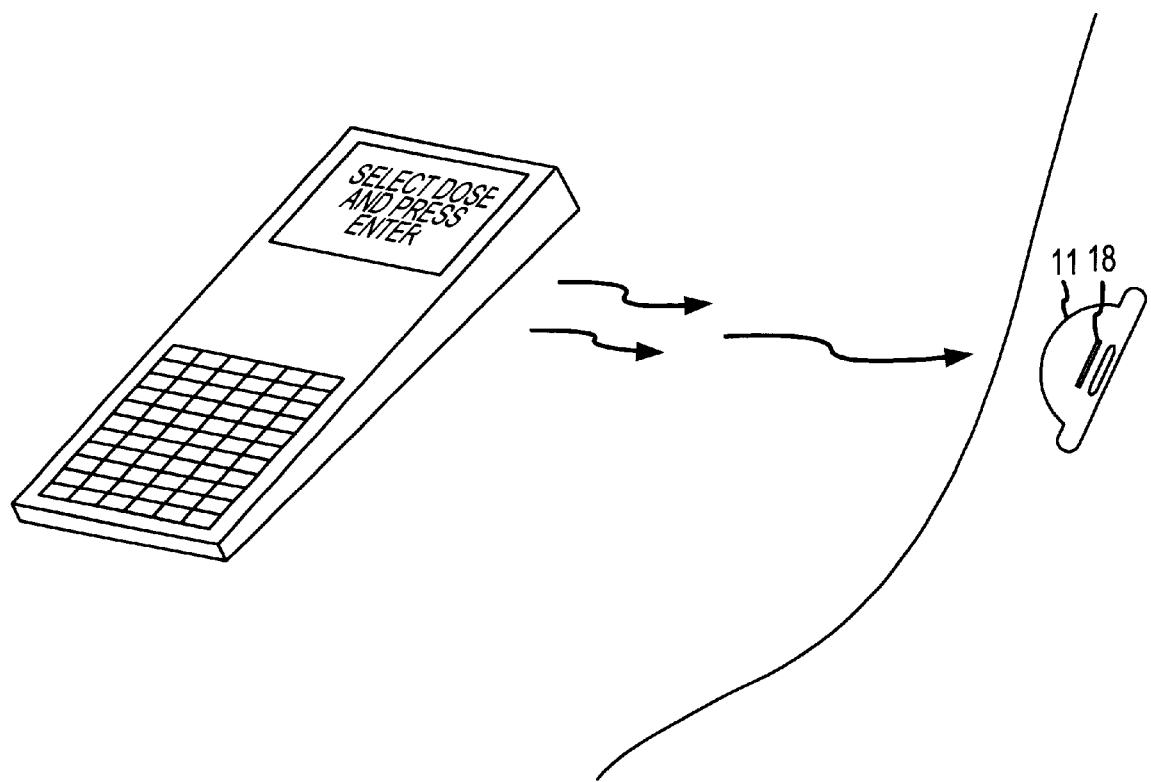
FIG. 1 is a perspective view illustrating a remotely powered embedded device of the active antisepsis device, constructed in accordance with the present invention, for treating subcutaneous implanted devices that receive power externally through a pick-up coil or internally through use of a battery.
Figure 2:
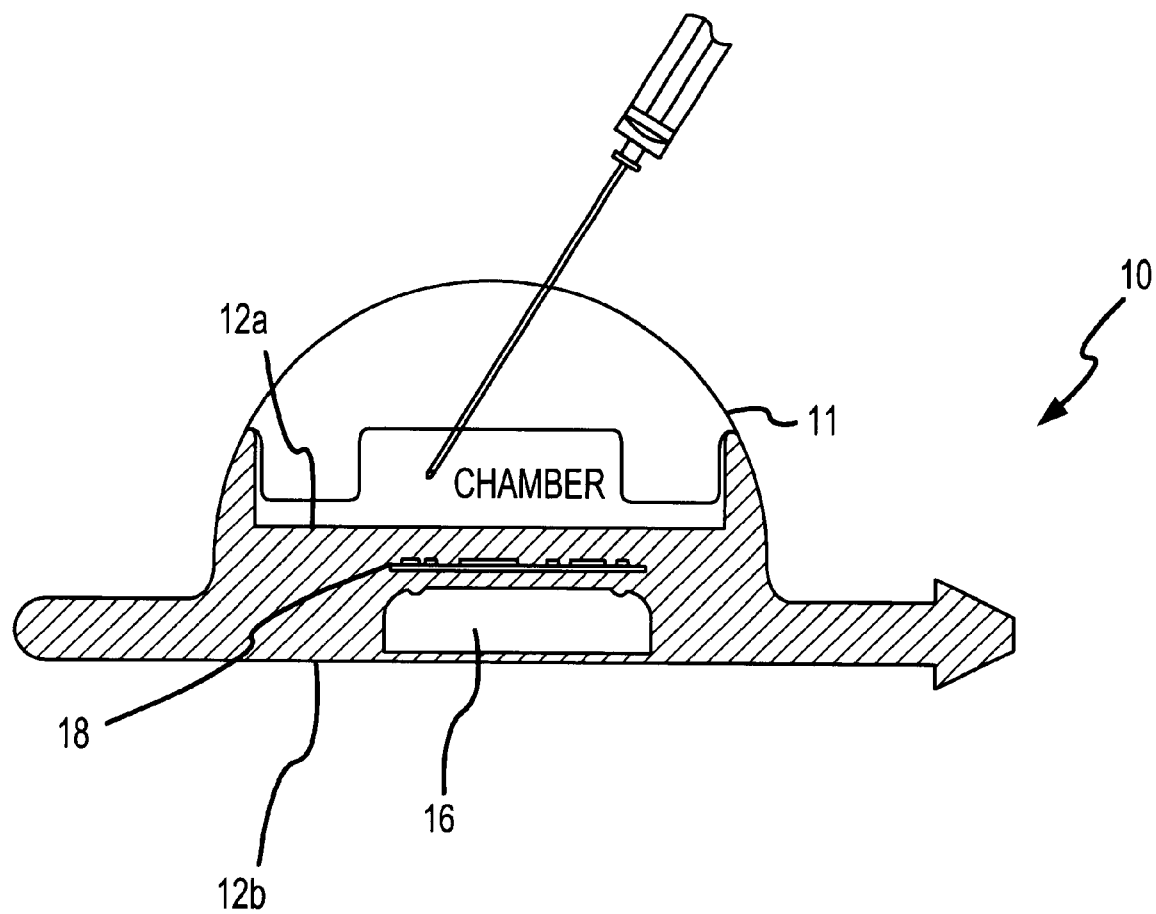
FIG. 2 is a sectional side view illustrating another embodiment of the active antisepsis device, constructed in accordance with the present invention, with a control system being mounted in a base of a port.
Figure 3:
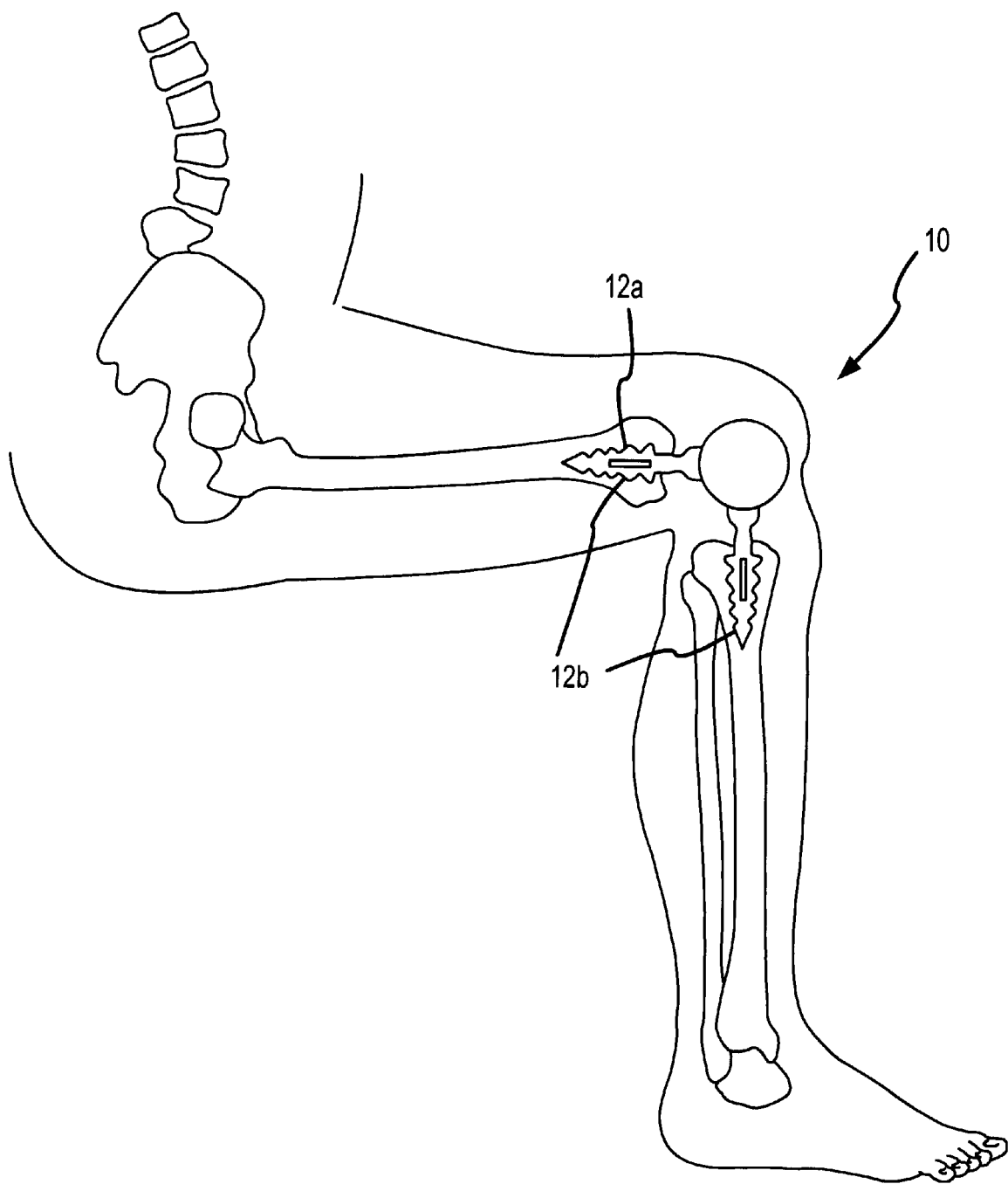
FIG. 3 is a sectional side view illustrating yet another embodiment of the active antisepsis device, constructed in accordance with the present invention, with the device being implanted in the bone attachments of an artificial knee joint.
Figure 4:
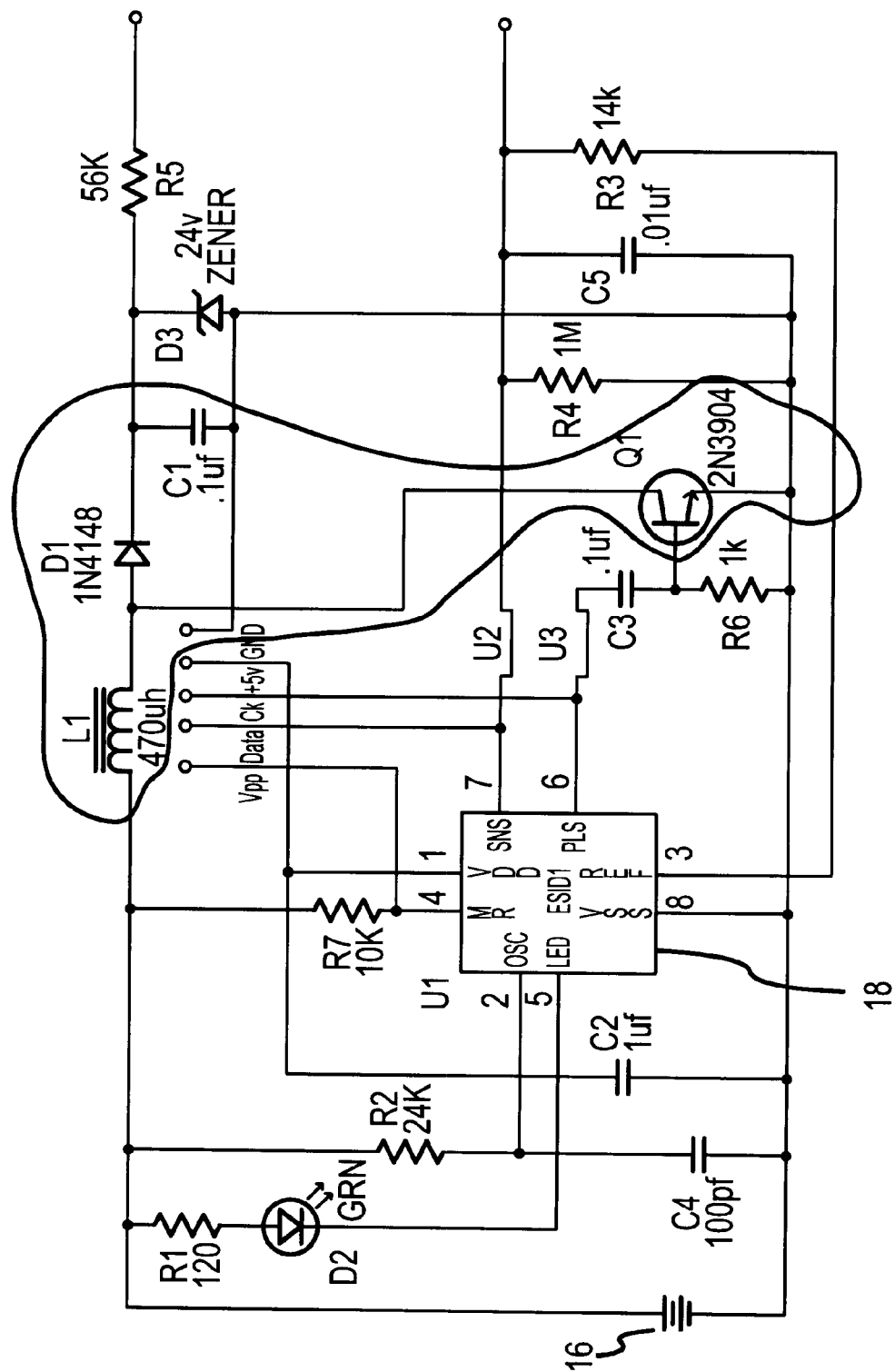
FIG. 4 is a schematic view illustrating the circuitry of the active antisepsis device, constructed in accordance with the present invention.
Figure 5:
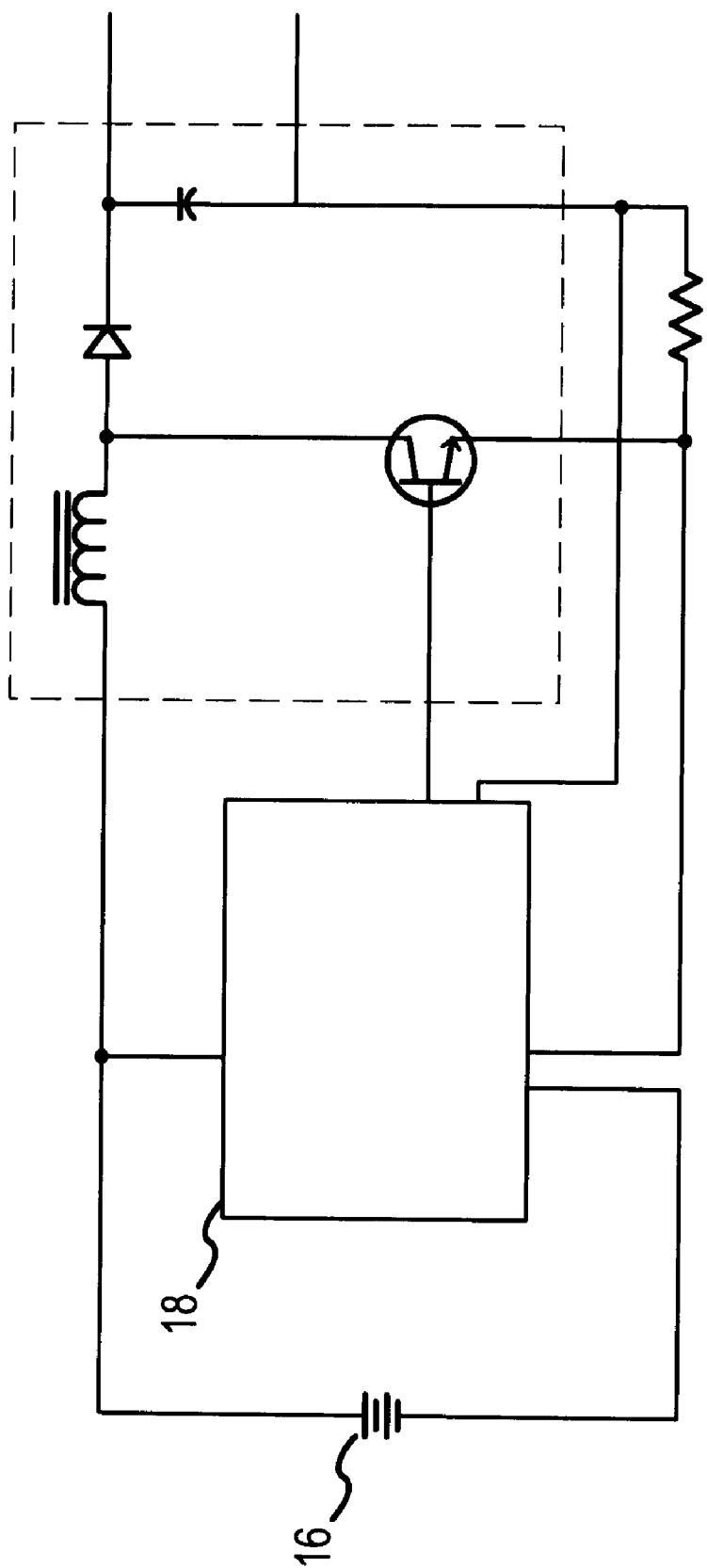
FIG. 5 is a block diagram illustrating the control system of the active antisepsis device, constructed in accordance with the present invention.
Figure 6:
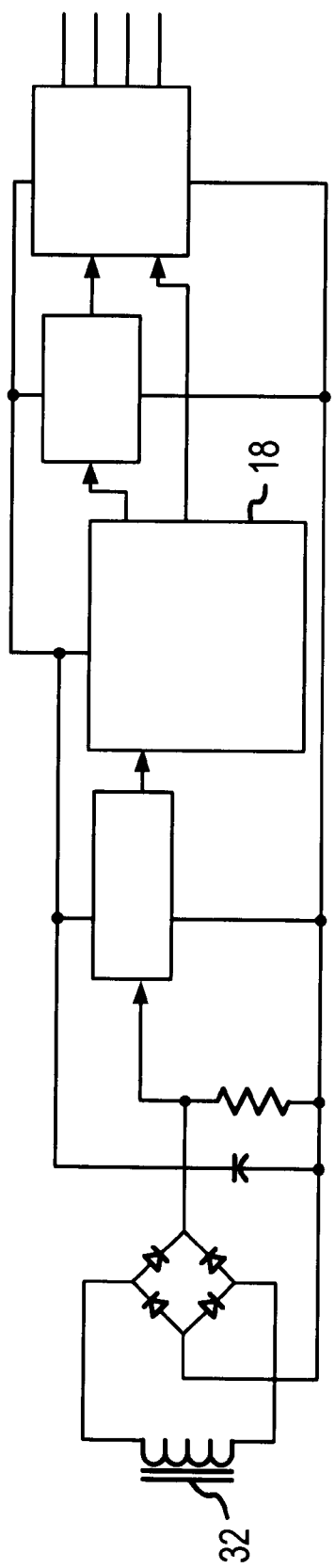
FIG. 6 is a block diagram illustrating the circuitry of the active antisepsis device, constructed in accordance with the present invention, with the power being delivered via a signal.
Figure 7:
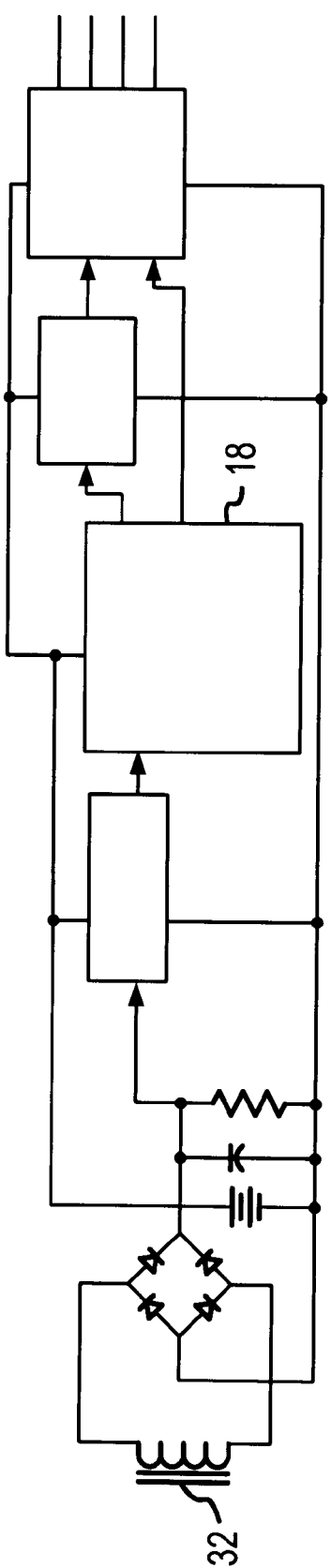
FIG. 7 is a block diagram illustrating the circuitry of the active antisepsis device, constructed in accordance with the present invention, with the power being delivered via a battery within the device.

As illustrated in FIGS. 1, 2, and 3, the present invention is an active antisepsis device, indicated generally at 10. The active antisepsis device 10 includes a housing 11 having a first active surface 12a and a second active surface 12b, which are contactable with the tissue and bodily fluids. Both the first active surface 12a and the second active surface 12b are actively driven. Preferably, the housing 11 is an implantable medical device and a system is electrically connected to the first active surface 12a and the second active surface 12b of the housing 11 creating an electric field between the various surfaces of the housing 11 through the body of a patient. An antimicrobial substance, such as silver, is attached to at least a portion of the first active surface 12a and the second active surface 12b with the substance being ionized upon application of the electric field thereby profusing the substance into the tissue.

The active antisepsis device 10 further has a power source 16 including, but not limited to, a battery, which powers a control system 18 for creating an electric field between the first active surface 12a and the second active surface 12b. As briefly mentioned above, the first active surface 12a and the second active surface 12b have a substance covering to be administered in an ionic form, or administered in a form that can be either disassociated, mobilized, or affected by means of the small electric field. Examples of the substance covering include, but are not limited to, Zinc, Silver, etc., since these substances have noted antimicrobial properties. With the substance covering on the first active surface 12a and the second active surface 12b, an enhanced and synergistic antimicrobial benefit or improvement is provided by killing or otherwise eliminating microorganisms including, but not limited to, virus, bacteria, fungus, etc. It should be noted that the first active surface 12a and the second active surface 12b can be constructed from the antimicrobial substance, coated with the antimicrobial substance, and/or used to profuse the antimicrobial substance.

The active antisepsis device 10 of the present invention contains the small power source 16 including, but not limited to a battery, which when applied to the first active surface 12a and the second active surface 12b causes an electric field to be carried through the tissue that is to be treated. The electric field can be any waveform that is advantageous to a particular therapy and can be unipolar or bipolar. An alternating field would serve to move ions from all active surfaces 12. The unipolar field would deliver the substance preferentially from an active surface and would drive the substance deeper into the tissue for therapies where subdermal interaction is required. The bipolar field would tend to leave the substance nearer to the device surface for applications that warrant a more surface protection than tissue penetrations as in the case of a urethral stint.

There can also be natural barriers to the diffusion as different tissues can sweep away the substance or block its flow entirely.

With the active antisepsis device 10 of the present invention, when the substance is profused electrolytically and the active surfaces are in reasonably close proximity, the electric field mobilizes, drives, or drags the substance through a region to the exit active surface 12. The electric field also tends to focus the flow of substance and allow a more even distribution as the depth into the tissue increases.

Experimentation by the Applicant of the present application has shown that using an active surface which is comprised of or coated with a silver compound in contact with an infected region of tissue, will profuse sufficient ionic silver into a region of tissue to attenuate the bacterial load by six (6) orders of magnitude ($10^6$) in less than one (1) hour. Various Preferred Embodiments of the Present Invention Remotely Powered Implantable As illustrated in FIGS. 1, 2, and 3, the infusion device 10 of the present invention is an implantable device 10 for long-term anti-microbial action or substance delivery. The first active surface 12a and the second active surface 12b of the implantable device 10 can be configured as described above in the other embodiments and the control of the field and polarity can be handled by an embedded microprocessor 18. The power can be coupled in by the application of a time-varying magnetic field to the exterior of the body. The magnetic field can be received by a coil 32 that is within or outside of the implantable device 10, rectified, and used by the circuitry to provide the electric field for the electrolytic profusion of the substance or the active surfaces 12. In this manner, very long-term therapy can be provided by periodically electrolytically profusing the substance of the active surfaces 12 through any developing biofilm, and into the tissue being treated killing colonizing bacteria in the region.

The generation of the waveforms of the infusion device 10 of the present invention can be controlled by a small microprocessor 18, such as a PIC12C5XX, requiring less than fifteen (15) microamps to operate. The microprocessor 18 can be procured in die form with dimensions of approximately 0.1 inch x approximately 0.1 inch and for a very low expense, the microprocessor 18 can easily be incorporated into the control system in a manner small enough to fit within a long-term indwelling medical device such as a CVC port, artificial joint, re-enforcing mesh, etc. With the microprocessor 10 of the active antisepsis device 10, the actual field strength can be monitored and integrated to allow the delivery of precise amounts of ionic substance at precise rates even though the ohmic contact to the region of interest will vary dramatically.

It should be noted that with the active antisepsis device 10 of the present invention, the actual dose must be correct over a wide range of different tissue impedances. For example, if too much silver is delivered to a region, the applied silver layer will be used up too quickly thus rendering the device ineffective to fight future infections. If too little silver is delivered to a region, the antimicrobial effect of the silver will not be sufficient to treat the infection. Alternatively, preferably, the electric field can be controlled by use of a constant current source, which is controlled by a fixed component value or profiled and modified by the microcontroller previously described.

The active antisepsis device 10 of the present invention goes beyond the present state of the art to actually deliver active antimicrobial silver ions, through an electrolytic means to the treatable region of interest. In doing so, the active antisepsis device 10 inhibits microorganism growth in the specific region of interest thereby inhibiting the need for systemic doses of antibiotics, in many cases. The active antisepsis device 10 of the present invention provides a better and more effective means of treatment for infection of indwelling devices as it is thousands of times more effective against the biofilms which plague these surfaces than any existing technique. The required micrograms of substance per milliliter of tissue can be achieved to the depths required to reach inside the colonies without relying on diffusion and capillary action. The total body-burden of the active agent can be one-hundred (1,000) to one thousand (10,000) times less than what would be expected for systemically administered antibiotics since the dose will be administered directly to the site.

Since the active antisepsis device 10 of the present invention causes the profusion of antimicrobial substances through the surface build up of fibrin sheath and the polysaccharide layer of the biofilms into a region that is defined by the active surface configuration, the infusion device 10 allows the beneficial effects of the substance to reach an region far greater than that of a simple impregnated device. A simple impregnated or coated device tends by its very nature to only protect the surface of the device and cannot penetrate the layers, which build up and support colonization of the infecting bacteria. Additionally, a device that is impregnated with an antimicrobial agent tends to hold onto the agent quite well and this renders the germicide far less effective as the virus or bacteria has limited exposure to it. The active antisepsis device 10 of the present invention, on the other hand, provides the smallest possible particles of the agent in an ionic form, which cause it to be readily bound to the germ causing more effective germicidal effects.

The present invention overcomes these foibles and introduces new capabilities to the art. The active antisepsis device 10 utilizes a small circuit based around a microcontroller. This system runs from very little power and thus can be powered for long periods of time by a battery or can be powered transcutaneously without direct electrical contact by an electromagnetic field. When battery is operated, the device 10 can "wake-up" periodically from a lower power sleep mode and activate its selected surfaces with waveforms and protocols programmed within the microcontroller 18. These treatments will drive antimicrobial silver ions through the slime layer, into the biofilm killing the colonizing bacteria more effectively than any other technique to date. Laboratory testing has showed this and has shown that a mere fifteen (15) minutes of activation every other day is sufficient to retard bacterial proliferation.

Large surface areas can be broken up into small active surfaces and activated individually to ensure homogenous distribution of the silver into the tissue at the required concentrations. This coordination and selective activation is accomplished by the microcontroller 18. This process of actively driving the generated silver ions into the surrounding tissue and ensures sufficient penetration in devices which exist within non-uniform environments.

The dose, rate, surface, treatment protocol, and waveform can be remotely controlled. The desired protocol is communicated to the microcontroller 18 by modulating the externally applied field, which is electromagnetically coupling energy to the device. The modulation carries information such as the protocol, dose, rate, and even desired surfaces to activate. The power supplied to the device 10 causes the system to "wake-up" and then the microcontroller 18 reads the information for its control by de-modulating the signal on the supplied power. This allows the device 10 to be implanted, which can be operated indefinitely as the power and treatment protocols can be provided externally through a non-interrupted skin boundary, which resists normal bacterial penetration.

In this manner, the antimicrobial silver is not only driven into the biofilm in an ionically activated state, but it is driven there only when need. Since the populations will double every twenty (20) minutes, it is not necessary to continuously maintain antimicrobial levels of silver in the surrounding tissues. The present invention as shown by laboratory tests to require activation at a level of less than fifteen (15) minutes every two days represents a 10,000 time reduction in the amount of silver required to coat the device. Or, when taken differently, will allow a very thin layer to last 10,000 times longer than normal passive elution.

This combination of driving active ions into the colony for more effective killing, coupled with the remote control and power delivery capabilities of the present invention, and the ability to select active surfaces to maximize effective coupling, renders the present invention superior to the present anti-infective coating technologies.

The foregoing exemplary descriptions and the illustrative preferred embodiments of the present invention have been explained in the drawings and described in detail, with varying modifications and alternative embodiments being taught. While the invention as been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements, which are disclosed herein.

What is claimed is:

1. A method of maintaining antisepsis in human body tissue, the method comprising:

wholly implanting within the tissue a device having (a) a first electrode of a first polarity with a first antimicrobial metal surface, (b) a second electrode of a second polarity opposite said first polarity, and (c) a power source in electrical communication with said first and second electrodes, whereby said first and second electrodes are in electrical communication with said tissue;

applying an electrical current from said power source through said first second electrodes and through said tissue; and electrolytically infusing antimicrobial metal ions from said antimicrobial metal surface into said tissue to maintain antisepsis in said tissue.

2. The method of claim 1, wherein said device further includes a microcontroller and further comprising controlling the delivery of said antimicrobial metal ions into said tissue with said microcontroller.

3. The method of claim 2, wherein said microcontroller is programmable by a radio frequency (RF) field applied from outside the body, and further comprising programming said microcontroller by applying said RF field from outside the body.

4. The method of claim 2, further comprising periodically applying said electrical current.

5. The method of claim 4, further comprising programming the microcontroller to vary said electrical current.

6. The method of claim 4, further comprising programming the microcontroller to vary an electrical waveform of said electrical current.

7. The method of claim 4, wherein said device has a plurality of first electrodes of a first polarity with antimicrobial surfaces positioned at a plurality of surface locations on the device, and further comprising programming the microcontroller to vary tissue locations at which antimicrobial ions are infused by switching between (a) applying an electrical current between said second electrode and a first set of at least one of said plurality of first electrodes, and (b) applying an electrical current between said second electrode and a second set of at least one of said first electrodes.

8. The method of claim 4, wherein said second electrode has a second antimicrobial metal surface, and further comprising applying a bipolar field between the first electrode and second electrode through said tissue to electrolytically infuse antimicrobial metal ions from both the first antimicrobial metal surface and the second antimicrobial metal surface into said tissue.

9. The method of claim 4, wherein said power source includes a rechargeable battery, and further comprising periodically recharging said battery by application of an electromagnetic field from outside the body.

10. The method of claim 4, wherein said device includes a prosthesis, and said step of electrolytically infusing antimicrobial metal ions includes infusing said antimicrobial metal ions proximate into tissue proximate the implanted prosthesis.

11. An apparatus for maintaining antisepsis in a human body, comprising:

(a) a housing having:
  (i) a first electrode of a first polarity with a first antimicrobial metal surface, and a second electrode of a second polarity opposite the first polarity;
  (ii) a power source in electrical communication with said first and second electrodes; and
  (iii) a microcontroller to control delivery of electrical current from said power source through said first and second electrodes to electrolytically infuse antimicrobial metal ions into body tissue; and (b) a controller external to said housing for placement outside the body, the controller being in radio frequency (RF) communication with the microcontroller for varying an electrical current delivery regimen through said first and second electrodes.

12. The apparatus of claim 11, wherein said microcontroller is RF programmable by said controller from outside the housing and outside the body to vary at least one of electrical current duration, period, voltage, current or waveform.

13. The apparatus of claim 11, wherein said power source is rechargeable, and further comprising a remote recharging source outside the housing for placement outside the body, the remote recharging source being in RF communication with the power source to recharge the power source by delivery of an RF signal through the body.

14. The apparatus of claim 11, wherein said housing includes an implantable prosthesis.

15. The apparatus of claim 14, wherein said implantable prosthesis is an artificial joint.

* * * * *